United States Patent [19]
Siochi

[11] Patent Number: 6,134,296
[45] Date of Patent: Oct. 17, 2000

[54] MICROGRADIENT INTENSITY MODULATING MULTI-LEAF COLLIMATOR

[75] Inventor: Ramon Alfredo Siochi, Fairfield, Calif.

[73] Assignee: Siemens Medical Systems, Inc., Iselin, N.J.

[21] Appl. No.: 09/234,364

[22] Filed: Jan. 20, 1999

[51] Int. Cl.[7] .................................................. A61N 5/10
[52] U.S. Cl. ................................................ 378/65; 378/901
[58] Field of Search ............................... 378/64, 65, 901

[56] References Cited

U.S. PATENT DOCUMENTS

| | | | |
|---|---|---|---|
| 5,602,892 | 2/1997 | Llacer | 378/65 |
| 5,663,999 | 9/1997 | Siochi | 378/65 |
| 6,038,283 | 3/2000 | Carol et al. | 378/65 |
| 6,052,430 | 4/2000 | Siochi et al. | 378/65 |

*Primary Examiner*—David V. Bruce

[57] ABSTRACT

The present invention provides for delivering two one (1) centimeter by point five (0.5) centimeter intensity maps that are orthogonal to each other so as to generate microgradients within each one centimeter by one centimeter square. Thus, an effective intensity map grid size is point five centimeters by point five centimeters.

15 Claims, 7 Drawing Sheets

$$b_m = a_m + \Delta H$$
$$c_m = a_m + \Delta V$$
$$d_m = a_m + \Delta H + \Delta V$$

$R_1$:

| 1 | 1 | 1 |
|---|---|---|
| 0 | 0 | 0 |
| 0 | 0 | 0 |

$R_2$:

| 0 | 0 | 0 |
|---|---|---|
| 1 | 1 | 1 |
| 0 | 0 | 0 |

$R_3$:

| 0 | 0 | 0 |
|---|---|---|
| 0 | 0 | 0 |
| 1 | 1 | 1 |

$C_1$:

| 1 | 0 | 0 |
|---|---|---|
| 1 | 0 | 0 |
| 1 | 0 | 0 |

$C_2$:

| 0 | 1 | 0 |
|---|---|---|
| 0 | 1 | 0 |
| 0 | 1 | 0 |

$C_3$:

| 0 | 0 | 1 |
|---|---|---|
| 0 | 0 | 1 |
| 0 | 0 | 1 |

| $m_{1,1}$ | $m_{1,2}$ | $m_{1,3}$ |
|---|---|---|
| $m_{2,1}$ | $m_{2,2}$ | $m_{2,3}$ |
| $m_{3,1}$ | $m_{3,2}$ | $m_{3,3}$ |

FIG. 9

MICROGRADIENT INTENSITY MODULATING MULTI-LEAF COLLIMATOR

BACKGROUND OF THE INVENTION

The present invention relates to a radiation emitting device, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist. The prescription is a definition of, for example, a particular volume and the level of radiation permitted to be delivered to that volume. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and delivered intensity levels to optimize the dose volume histograms, which define a cumulative level of radiation which is to be delivered to a specified volume. Typical optimization engines optimize the dose volume histograms by considering the oncologist's prescription, or three-dimensional specification of dosage to be delivered. In such optimization engines, the three-dimensional volume is broken into cells, each cell defining a particular level of radiation to be administered. The outputs of the optimization engines are intensity maps, which are determined by varying the intensity at each "cell" in the map. The intensity maps specify a number of fields defining desired (optimized) intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation, borders between critical structures and tumor volumes are sometimes not well approximated with a standard collimator leaf. A standard collimator leaf is approximately one (1) centimeter square. Typically, then, a one centimeter by one centimeter grid size or cell size is provided over the intensity map. However, at times a higher resolution (for example five millimeters by five millimeters) may be preferable. Known solutions to this problem include introducing new hardware such as collimators with thinner leaves. However, this introduction of new hardware is an expensive solution which adds weight to the treatment head and can decrease reliability and life time. Moreover, addition of such collimator can reduce clearance between the treatment head and the patient.

Accordingly there is a need for system and method for achieving higher spatial resolution intensity modulation without changing current multi-leaf collimator leaf widths.

SUMMARY OF THE INVENTION

These and other drawbacks in the prior art are overcome in large part by a system and method according to the present invention. In particular, the present invention provides for delivering two one (1) centimeter by point five (0.5) centimeter intensity maps that are orthogonal to each other so as to generate microgradients within each one centimeter by one centimeter square. Thus, an effective intensity map grid size is point five centimeters by point five centimeters.

BRIEF DESCRIPTION OF THE DRAWINGS

A better understanding of the present invention can be obtained when the following detailed description is considered in conjunction with the following drawings in which:

FIG. 8 is an exemplary orthogonal delivery map for a three by three microcell; and FIG. 9 is a representation of three by three microcells in a macrocell.

DETAILED DESCRIPTION OF THE INVENTION

Figure 1:
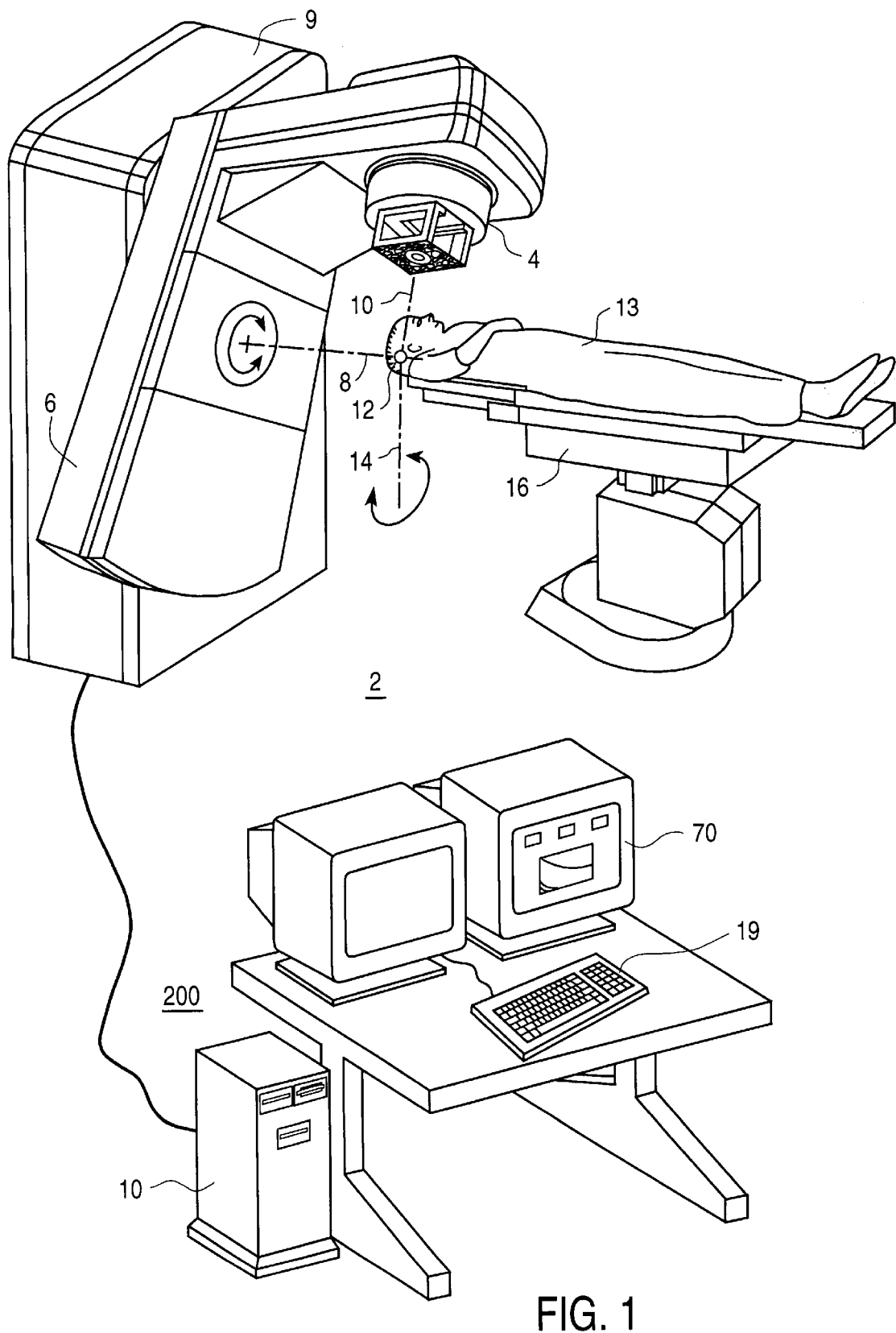
FIG. 1 is a diagram of a radiation treatment device and treatment console according to an embodiment of the present invention.

Referring to the drawings and especially to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such as a data storage device. Various data can be displayed before and during the treatment on the screen of the monitor 70.

Figure 2:
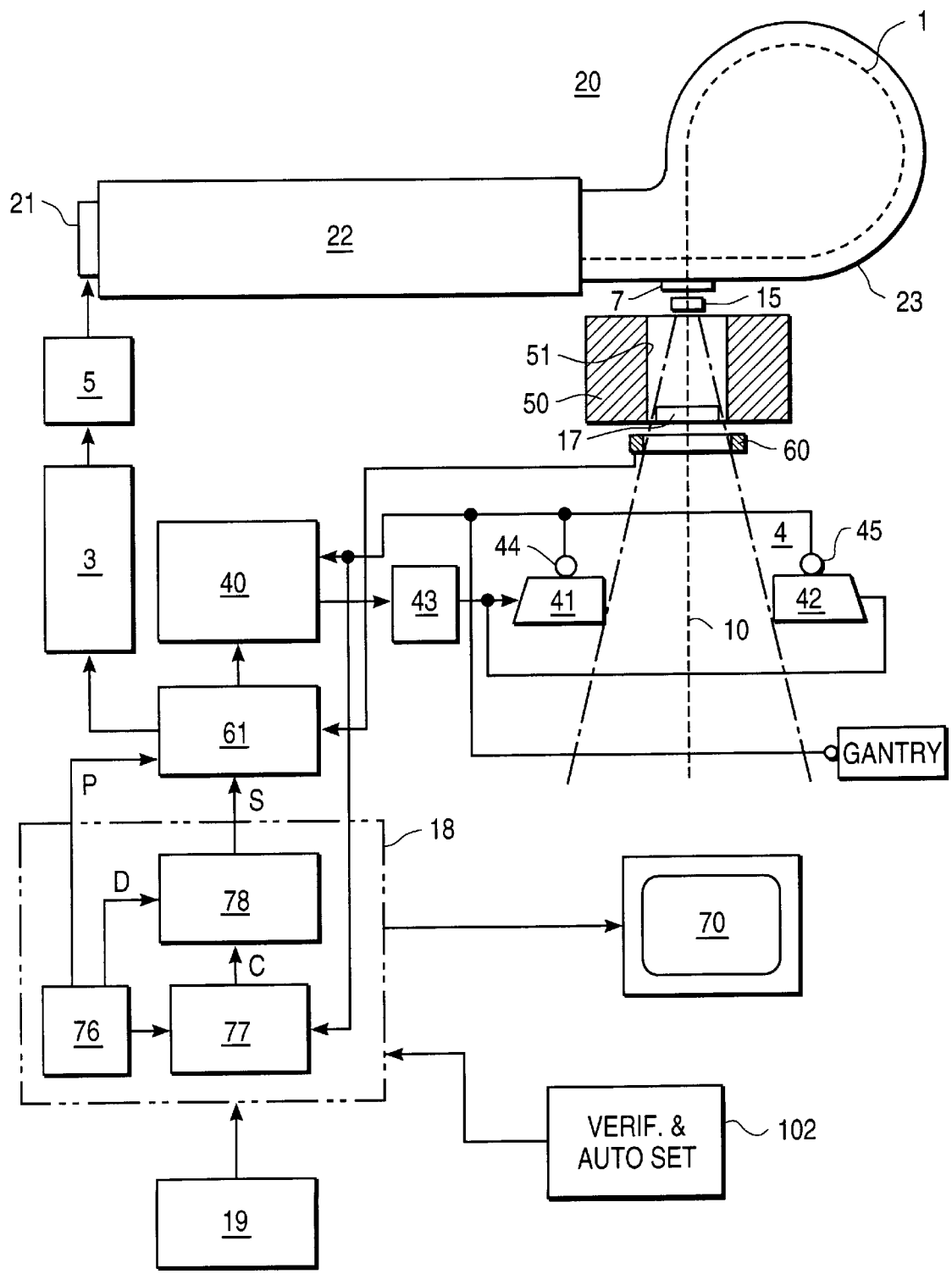
FIG. 2 is a more detailed block diagram illustrating portions of the present invention

Turning now to FIG. 2, a block diagram of the radiation treatment device 2 and portions of the treatment unit 200 are illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source (not shown) is provided, which supplies radio frequency signals for the generation of an electromagnetic field supplied to the wave guide 22. The electrons injected by the injector 5 and emitted by the electron gun 21 are accelerated by this electromagnetic field in the wave guide 22 and exit at the end opposite to electron gun 21 in electron beam 1. The electron beam 1 then enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 includes a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 2 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions. As discussed above, the plate arrangement 401 may alternatively include a multi-leaf collimator having many radiation blocking leaves.

Figure 3:
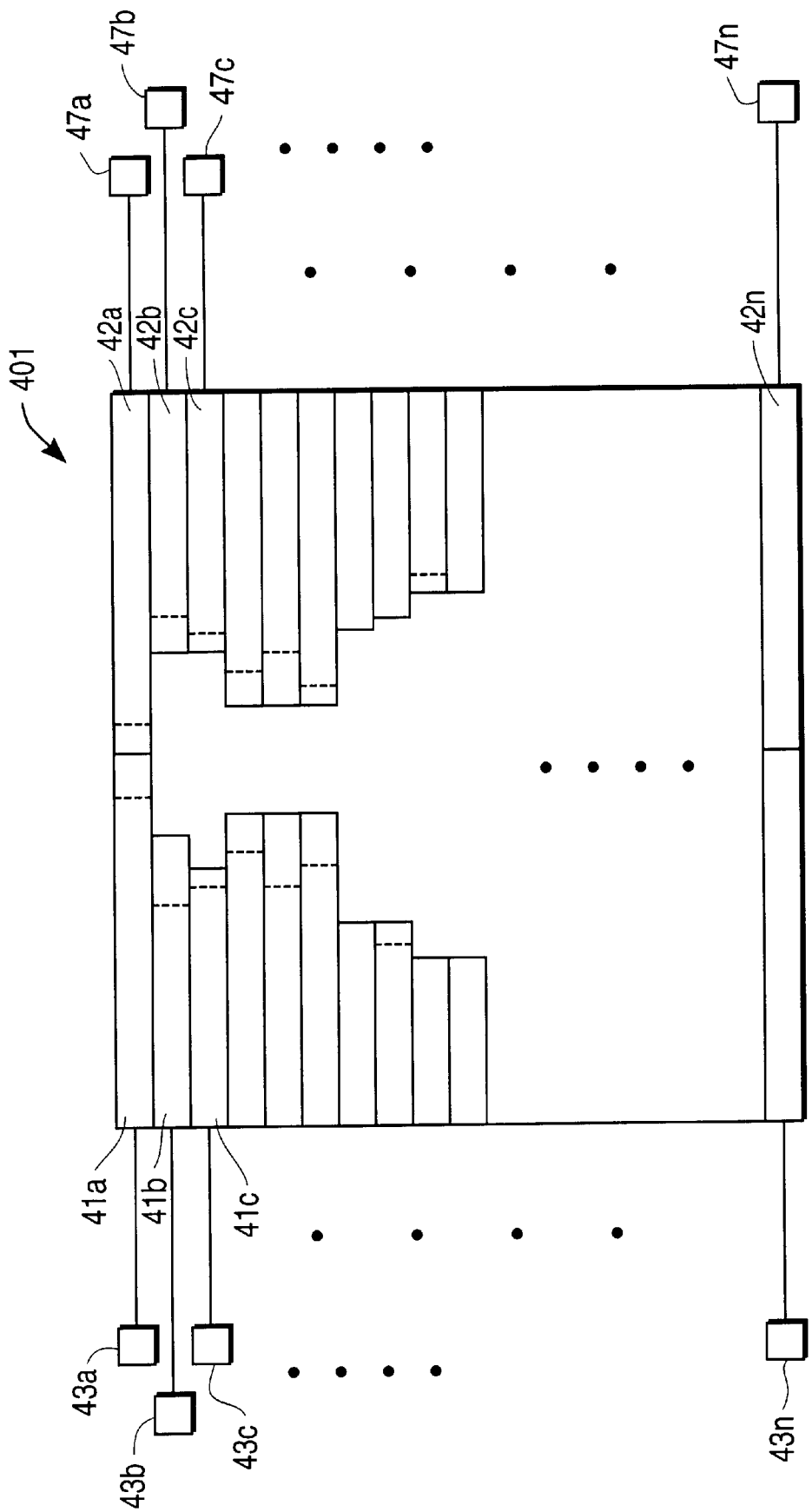
FIG. 3 is a diagram of a multi-leaf collimator according to an embodiment of the invention.

The leaves of such a multi-leaf collimator are illustrated in greater detail in FIG. 3. Opposing leaf, or rod pairs 41a–41n, 42a–42n, each include a motor or drive unit 43a–43n, and 47a–47n, respectively. The drive units drive the rods, or leaves, in and out of the treatment field, thus creating the desired field shape. The rods, or leaves, are relatively narrow, and typically cast a shadow of about 1 cm at isocenter.

Turning back to FIG. 2, the motor controller 40 is coupled to a dose unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. In such a radiation device, the dose absorbed by the object 13 is dependent upon movement of the collimator leaves.

The central processing unit 18 is programmed by the therapist according to the instructions of the oncologist. The delivery of the radiation treatment is input through a keyboard 19. The central processing unit 18 is further coupled to a dose control unit 61 that generates the desired values of radiation for controlling trigger system 3. The trigger system 3 then adapts the pulse radiation frequency and other parameters in a corresponding, conventional manner. The central processing unit 18 further includes a control unit 76 which controls execution of the program and the opening and closing of the collimator plates 41, 42 according to the present invention to deliver radiation according to a desired intensity profile.

Figure 4:
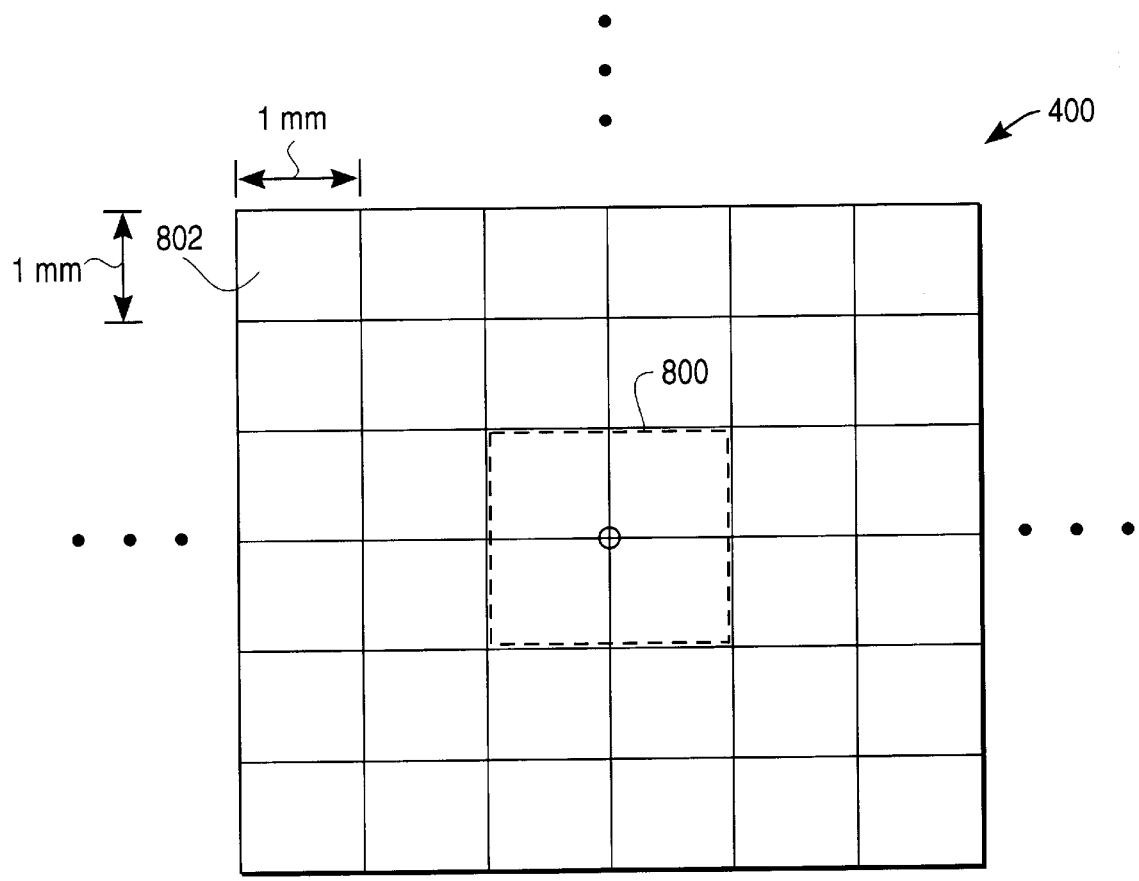
FIG. 4 is a diagram illustrating exemplary microcells in an intensity map.

The central processing unit 18 and, particularly, the control unit 76 controls optimization and mapping of an intensity map according to the present invention. In particular, FIG. 4 is a representation of an intensity map 400 having a plurality of 1 cm×1 cm of macrocells 800 (represented by the dashed lines) and plurality of five millimeter by five millimeter (5 mm×5 mm) microcells 802. As noted above, the exemplary multi-leaf collimator has a leaf width of one centimeter shadow at isocenter. According to the present invention, fields that are ninety degrees offset from each other in collimator rotation are combined, and a grid size of one centimeter by five millimeters for the leaf positions are permitted. To form microgradients within the one centimeter by one centimeter cells 800, each one centimeter by one centimeter cell is made up of four 5 millimeter by 5 millimeter microcells. Thus, as shown in FIG. 4, an exemplary cell intensity map with each microcell in the map measuring five millimeters by five millimeters is shown. It is noted that only a six by six grid is shown for simplicity; according to one embodiment, the intensity map is forty-two by forty-two. In that embodiment, the center of the intensity is shown at point 402 which is the corner shared by the cells at row and column locations of (21,21), (21,22), (22,21), (22,22). Each four of these five millimeter by five millimeter microcells is grouped into one centimeter by one centimeter cells such as cell 404 resulting in a new matrix that is twenty-one rows by twenty-one columns with the isocenter being inside the cell in row eleven, column eleven.

Figure 5:
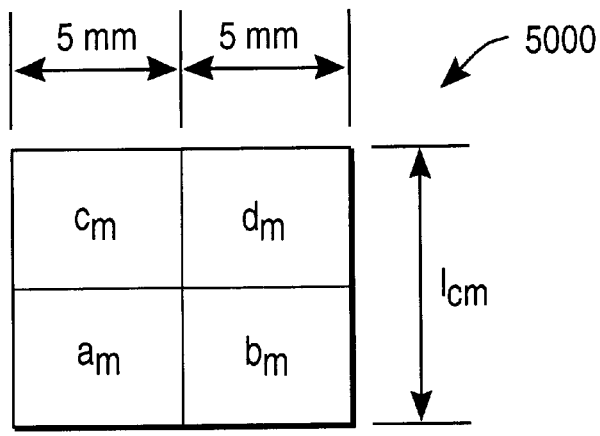
FIG. 5 illustrates exemplary mapping of the microcells.

FIG. 5 illustrates an exemplary mapping 5000 of the microcells. Microcell a is the cell with the minimum value, b is the microcell in the same row as a, c is the microcell in the same column as a and d is the microcell diagonally across from a. Then the following requirements are necessary for the forty-two by forty-two map (i.e., micromap) to be deliverable with a one centimeter leaf width multi-leaf collimator:

$$b_m = a_m + \Delta H$$
$$c_m = a_m + \Delta V$$
$$d_m = a_m + \Delta H + \Delta V$$

Figure 6A:
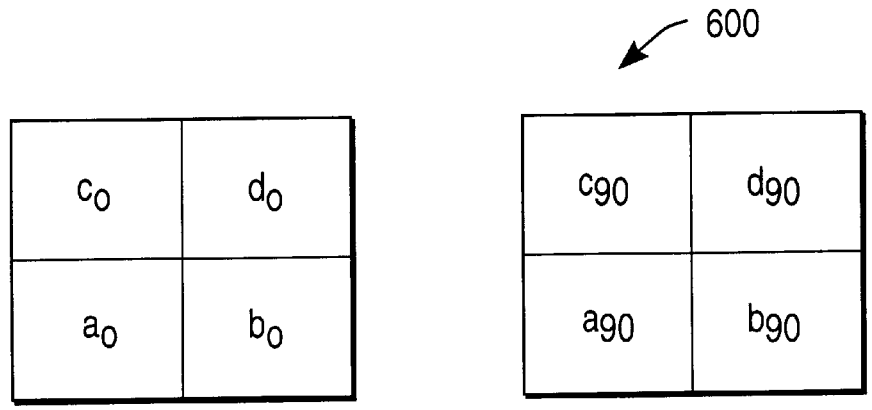
FIG. 6a and FIG. 6b illustrate exemplary orthogonal mapping of the microcell of FIG. 5.

$\Delta H$ and $\Delta V$ are arbitrary increments. Having defined the microcells, it is now necessary to decompose the microcells into two orthogonal maps. If the counterparts of the cells of positions a, b, c and d (whose values are $a_m$, $b_m$, $c_m$, $d_m$) in the micromap with the cells in the two orthogonal maps as $a_0$, $b_0$, $c_0$, and $d_0$ for the map that has the same collimator setting as the micromap, and $a_{90}$, $b_{90}$, $c_{90}$, and $d_{90}$ for the map that is off set by 90 degrees (as shown in FIG. 6a), then the decomposed values map as shown in Equation 2.

$$a_0 = c_0 = a_m$$
$$b_0 = d_0 = b_m$$
$$a_{90} = b_{90} = 0$$
$$c_{90} = d_{90} = \Delta V$$

Figure 6B:
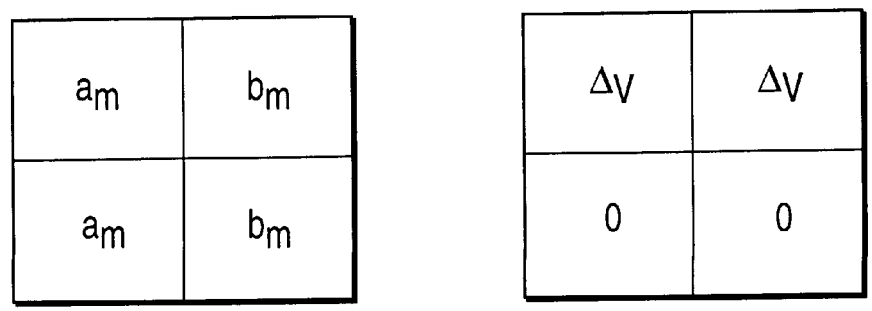

This is illustrated more clearly with regard to FIG. 6b.

As can be appreciated, although the orthogonal maps are represented as five millimeter by five millimeter maps, they are decomposed into maps having one centimeter by five millimeter and five millimeter by one centimeter cell sizes. Once the one centimeter by five millimeter maps have been generated they can be segmented with traditional methods and in particular using the optimization method described in commonly assigned U.S. Pat. No. 5,663,999, which is hereby incorporated by reference in its entirety as if fully set forth herein.

It is noted that a similar mapping and division may be provided if higher resolution is desired. For example, each macrocell may be directed into nine (3×3) microcells. In that case, such an intensity map may be deliverable as two orthogonal intensity maps with a resolution of 1 cm×⅓ cm and ⅓ cm×1 cm. For example, turning to FIG. 8, microcell values for each macrocell can be delivered as a linear combination of six 3×3 single row ($R_1$–$R_3$) or single column ($C_1$–C) matrices. If each macrocell $M_{ij}$ (where I and j have values from 1–21) is represented as in FIG. 9, then to be able to deliver an intensity map with a resolution of a microcell, each macrocell must meet the requirement of Equation 3:

$$M_{i,j} = \sum_p (r_p R_p + c_p C_p) \tag{3}$$

where p is the index of microcells in a row, $r_p$ and $c_p$ are whole numbers (0, 1, 2 . . . ) and $R_p$ and $C_p$ are the single row and column micromatrices. The two orthogonal maps are defined as follows:

$$M_{0i,j} = \sum_p c_p C_p \tag{4}$$
$$M_{90i,j} = \sum_p r_p R_p$$

In a 3×3 micromatrix, the maximum value of index p is 3. It is noted that Equations 3 and 4 apply generally to even smaller sized microcells: Cp is the micromatrix whose pth column has all 1's (0's elsewhere) and Rp is the micromatrix whose pth row has all 1's (0's elsewhere).

Figure 7:
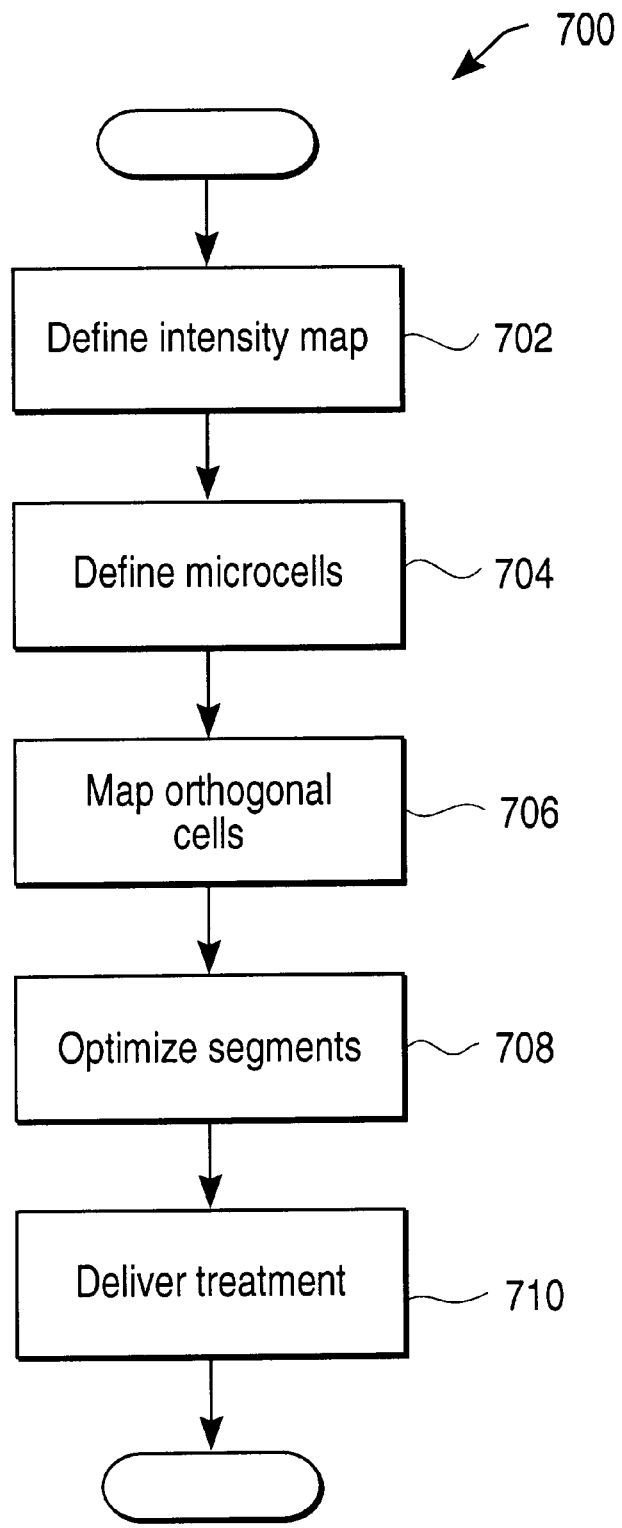
FIG. 7 is a flowchart illustrating a method according to the present invention.

A flowchart illustrating this process is shown in FIG. 7. In particular, in step 702 the intensity map for the treatment delivery is defined in the control unit. In a step 704, a plurality of microcells centering around an isocenter 402 is defined and stored. The microcells may be, for example, 0.5 centimeter×0.5 centimeter microcells within 1 centimeter×1 centimeter "macrocells". In a step 706, the microcells are mapped into two orthogonal segments as defined in Equations 1 and 2. Next, in step 708 the segments may be optimized according to U.S. Pat. No. 5,663,999. Finally, in step 710, the treatment is delivered. It is noted that smaller sized microcells may be achieved as described with regard to Equations 3, 4 and FIG. 9.

The invention described in the above detailed description is not intended to be limited to the specific form set forth herein, but is intended to cover such alternatives, modifications, and equivalents as can reasonably be included within the spirit and scope of the appended claims.

What is claimed is:

1. A method for delivering radiation from a source to a body, comprising:
    defining an intensity map of radiation to be delivered, said intensity map including a plurality of cells of a first size;
    dividing said intensity into cells of a second size;
    mapping a plurality of said cells of a second size into orthogonal cells; and
    delivering said radiation based on a result of said mapping.

2. A method according to claim 1, said cells of a first size having at least a first dimension approximately equal to a width of a collimator leaf.

3. A method according to claim 2, said cells of a second size having at least a first dimension approximately half of said width of said collimator leaf.

4. A method according to claim 1, further including optimizing delivery of said orthogonal cells.

5. A method according to claim 3, wherein said cells of said first size are approximately 1 cm×1 cm.

6. A method according to claim 5, wherein said cells of said second size are 5 mm×5 mm.

7. A method according to claim 6, wherein said dividing includes dividing each cell of said first size into four cells of said second size according to the following:

$$b_m = a_m + \Delta H$$
$$c_m = a_m + \Delta V$$
$$d_m = a_m + \Delta H + \Delta V.$$

8. A method according to claim 7, wherein said mapping includes mapping according to the following:

$$a_0 = c_0 = a_m$$
$$b_0 = d_0 = b_m$$
$$a_{90} = b_{90} = 0$$
$$c_{90} = d_{90} = \Delta V.$$

9. A system for delivering radiation from a source to an object, comprising:
- a collimator having multiple leaves for blocking radiation from said source, said leaves having a first predetermined width;
- means for specifying an intensity map, said intensity map defining a plurality of cells having said first predetermined width;
- means for deriving a second intensity map from said intensity map, said deriving including defining microcells having a width a predetermined portion of said first predetermined width; and
- means for delivering said radiation according to an orthogonal mapping of said microcells.

10. A system according to claim 9, said specifying means specifying 1 cm×1 cm cells.

11. A system according to claim 10, said deriving means deriving 5 mm×5 mm microcells.

12. A system according to claim 11, said deriving means deriving said microcells according to the following:

$$b_m = a_m + \Delta H$$
$$c_m = a_m + \Delta V$$
$$d_m = a_m + \Delta H + \Delta V.$$

13. A system according to claim 12, said delivering means delivering said radiation according to the following:

$$a_0 = c_0 = a_m$$
$$b_0 = d_0 = b_m$$
$$a_{90} = b_{90} = 0$$
$$c_{90} = d_{90} = \Delta V.$$

14. A method according to claim 1, wherein said plurality of cells of a second size are mapped according to the following:

$$M_{i,j} = \sum_p (r_p R_p + c_p C_p)$$

where $M_{i,j}$ is a macrocell, p is the index of a microcell, I and j are the number of macrocells in the row and column directions, respectively, $R_p$ and $C_p$ are single row and single column micromatrices, and $r_p$ and $c_p$ are whole numbers.

15. A system according to claim 9, wherein said mapping is defined by the following:

$$M_{i,j} = \sum_p (r_p R_p + c_p C_p)$$
$$M_{0i,j} = \sum_p r_p R_p$$
$$M_{90i,j} = \sum_p c_p R_p$$

where $M_{i,j}$ is a macrocell, p is the index of a microcell, I and j are the number of macrocells in the row and column directions, respectively, $R_p$ and $C_p$ are single row and single column micromatrices, and $r_p$ and $c_p$ are whole numbers.

* * * * *